United States Patent
Biedermann et al.

(10) Patent No.: US 9,451,988 B2
(45) Date of Patent: Sep. 27, 2016

(54) ROD-SHAPED IMPLANT IN PARTICULAR FOR STABILIZING THE SPINAL COLUMN AND STABILIZATION DEVICE INCLUDING SUCH A ROD-SHAPED IMPLANT

(75) Inventors: Lutz Biedermann, VS-Villingen (DE); Jürgen Harms, Karlsruhe (DE); Helmar Rapp, Deißlingen (DE); Berthold Dannecker, St. Georgen (DE)

(73) Assignee: Biedermann Technologies GmbH & Co. KG, Donauschingen (DE)

(*) Notice: Subject to any disclaimer, the term of this patent is extended or adjusted under 35 U.S.C. 154(b) by 587 days.

(21) Appl. No.: 12/550,960

(22) Filed: Aug. 31, 2009

(65) Prior Publication Data

US 2010/0087863 A1 Apr. 8, 2010

Related U.S. Application Data

(60) Provisional application No. 61/094,207, filed on Sep. 4, 2008.

(30) Foreign Application Priority Data

Sep. 4, 2008 (EP) .................................. 08 015 662

(51) Int. Cl.
*A61B 17/70* (2006.01)

(52) U.S. Cl.
CPC ....... *A61B 17/7029* (2013.01); *A61B 17/7031* (2013.01); *A61B 17/7035* (2013.01); *A61B 17/7037* (2013.01); *A61B 17/7032* (2013.01)

(58) Field of Classification Search
CPC .................................. A61B 17/7014–17/7031

USPC ................. 606/246, 251–252, 257, 261–262
See application file for complete search history.

(56) References Cited

U.S. PATENT DOCUMENTS

| | | | |
|---|---|---|---|
| 8,043,340 B1* | 10/2011 | Law | 606/257 |
| 2004/0049190 A1 | 3/2004 | Biedermann et al. | |
| 2005/0065516 A1 | 3/2005 | Jahng | |
| 2005/0085815 A1* | 4/2005 | Harms et al. | 606/61 |
| 2005/0124991 A1 | 6/2005 | Jahng | |

(Continued)

FOREIGN PATENT DOCUMENTS

| | | |
|---|---|---|
| EP | 0 669 109 B1 | 8/1995 |
| EP | 1 757 243 A1 | 2/2007 |

(Continued)

OTHER PUBLICATIONS

European Search Report dated Nov. 28, 2008 for European Application No. 08015662.3, Applicant Biedermann Motech GmbH, European Search Report mailed Dec. 8, 2008 (6 pgs.)

*Primary Examiner* — Eduardo C Robert
*Assistant Examiner* — Michelle C Eckman
(74) *Attorney, Agent, or Firm* — Lewis Roca Rothgerber Christie LLP

(57) ABSTRACT

A rod-shaped implant for stabilizing bone structures, in particular the spinal column includes a rod-shaped implant having a rod-shaped member with a first end and a second and a longitudinal axis. The rod-shaped member is at least partly made from a plastic material exhibiting flexibility and includes a longitudinal bore. A reinforcing rod is accommodated in the bore and is made from a material which is more rigid than the material of the rod-shaped member itself. The reinforcing rod is slidable in the bore.

20 Claims, 4 Drawing Sheets

(56) References Cited

U.S. PATENT DOCUMENTS

| | | | |
|---|---|---|---|
| 2005/0149020 A1 | 7/2005 | Jahng | |
| 2005/0154390 A1 | 7/2005 | Biedermann et al. | |
| 2005/0203513 A1 | 9/2005 | Jahng et al. | |
| 2005/0203517 A1 | 9/2005 | Jahng et al. | |
| 2005/0203519 A1* | 9/2005 | Harms et al. | 606/61 |
| 2006/0058788 A1* | 3/2006 | Hammer et al. | 606/61 |
| 2006/0149228 A1 | 7/2006 | Schlapfer et al. | |
| 2006/0247638 A1 | 11/2006 | Trieu et al. | |
| 2006/0247779 A1* | 11/2006 | Gordon et al. | 623/17.15 |
| 2006/0264935 A1* | 11/2006 | White | 606/61 |
| 2007/0005063 A1* | 1/2007 | Bruneau et al. | 606/61 |
| 2007/0042633 A1 | 2/2007 | Frigg et al. | |
| 2007/0049937 A1 | 3/2007 | Matthis et al. | |
| 2007/0055244 A1 | 3/2007 | Jackson | |
| 2007/0093820 A1 | 4/2007 | Freudiger | |
| 2007/0118122 A1* | 5/2007 | Butler et al. | 606/61 |
| 2007/0129729 A1* | 6/2007 | Petit et al. | 606/61 |
| 2007/0198088 A1 | 8/2007 | Biedermann et al. | |
| 2007/0225710 A1* | 9/2007 | Jahng et al. | 606/61 |
| 2007/0233064 A1 | 10/2007 | Holt | |
| 2007/0233073 A1 | 10/2007 | Wisnewski et al. | |
| 2008/0021469 A1 | 1/2008 | Holt | |
| 2008/0082103 A1* | 4/2008 | Hutton et al. | 606/73 |
| 2008/0125777 A1 | 5/2008 | Veldman et al. | |
| 2008/0154307 A1* | 6/2008 | Colleran et al. | 606/257 |
| 2008/0183212 A1 | 7/2008 | Veldman et al. | |
| 2008/0183213 A1* | 7/2008 | Veldman et al. | 606/257 |
| 2008/0234746 A1* | 9/2008 | Jahng et al. | 606/278 |
| 2008/0255617 A1* | 10/2008 | Cho et al. | 606/246 |
| 2008/0269804 A1 | 10/2008 | Holt | |
| 2009/0054932 A1* | 2/2009 | Butler et al. | 606/255 |
| 2009/0093844 A1* | 4/2009 | Jackson | 606/254 |
| 2009/0099608 A1* | 4/2009 | Szczesny | 606/257 |
| 2009/0234388 A1* | 9/2009 | Patterson et al. | 606/246 |
| 2009/0259257 A1* | 10/2009 | Prevost | 606/255 |
| 2009/0275983 A1* | 11/2009 | Veldman et al. | 606/258 |
| 2009/0326582 A1* | 12/2009 | Songer et al. | 606/255 |
| 2009/0326584 A1* | 12/2009 | Slivka et al. | 606/261 |
| 2010/0204736 A1* | 8/2010 | Biedermann et al. | 606/264 |
| 2010/0211105 A1* | 8/2010 | Moumene et al. | 606/258 |
| 2010/0318130 A1* | 12/2010 | Parlato et al. | 606/254 |
| 2011/0029022 A1* | 2/2011 | Zehnder et al. | 606/264 |
| 2011/0251648 A1* | 10/2011 | Fiechter et al. | 606/286 |

FOREIGN PATENT DOCUMENTS

| | | |
|---|---|---|
| EP | 1 795 134 A1 | 6/2007 |
| EP | 1 891 904 A1 | 2/2008 |
| EP | 1 900 334 A1 | 3/2008 |
| WO | WO 2004/096066 A2 | 11/2004 |
| WO | WO 2005/084566 A1 | 9/2005 |
| WO | WO 2006/118866 A1 | 11/2006 |
| WO | WO 2007/097905 A2 | 8/2007 |
| WO | WO 2007/109431 A2 | 9/2007 |

* cited by examiner

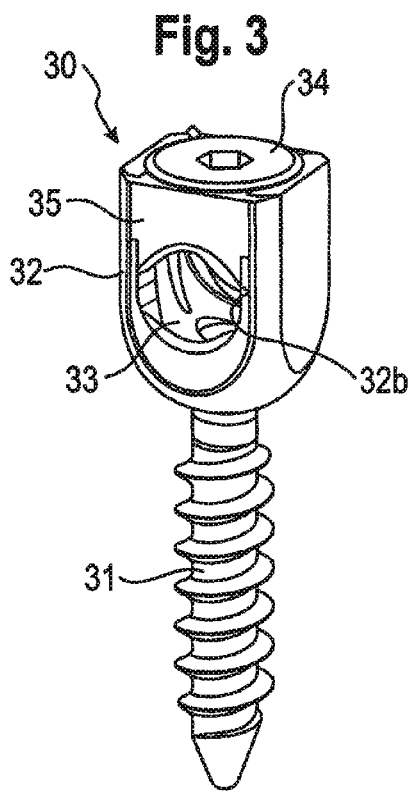
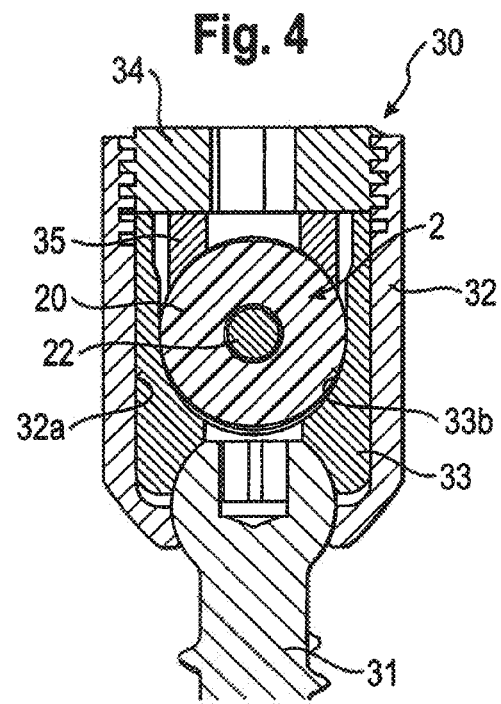
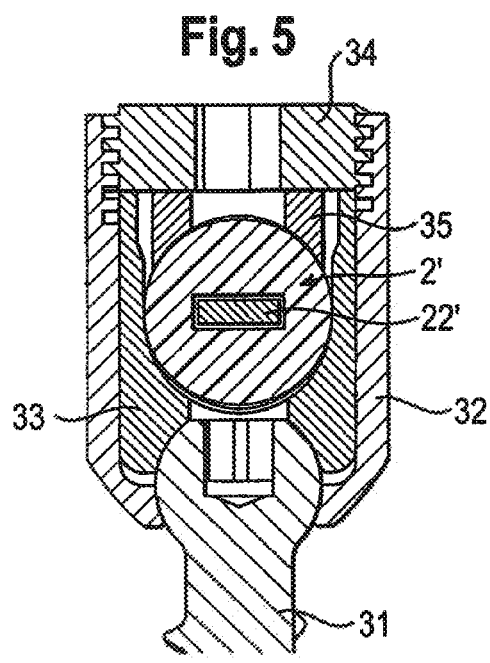
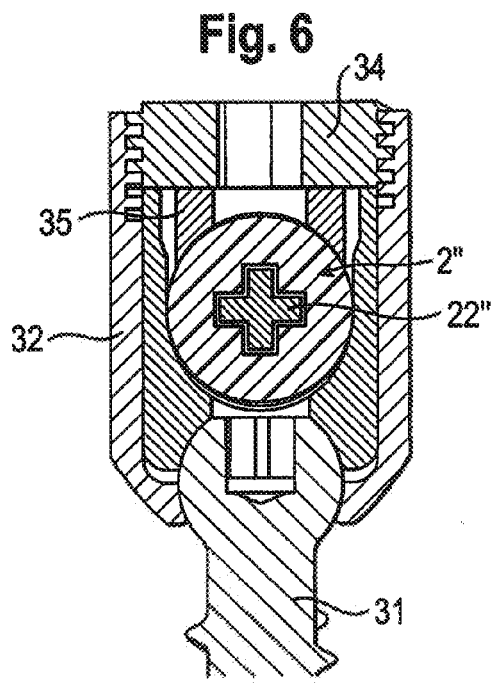

ROD-SHAPED IMPLANT IN PARTICULAR FOR STABILIZING THE SPINAL COLUMN AND STABILIZATION DEVICE INCLUDING SUCH A ROD-SHAPED IMPLANT

CROSS-REFERENCE TO RELATED APPLICATION(S)

The present application claims the benefit of U.S. Provisional Patent Application Ser. No. 61/094,207, filed Sep. 4, 2008, the contents of which are hereby incorporated by reference in their entirety, and claims priority from European Patent Application EP 08 015 662.3, filed Sep. 4, 2008, the contents of which are hereby incorporated by reference in their entirety.

BACKGROUND

The application relates to a rod-shaped implant in particular for stabilizing the spinal column and to a spinal stabilization device including such a rod-shaped implant.

EP 0 669 109 B1 discloses a stabilizing apparatus for stabilizing neighbouring thoracic vertebrae. The apparatus includes two monaxial pedicle screws and a strap that is fixed in the receiver member of each pedicle screw by means of a clamping screw and a support element that is mounted on the strap and is designed as a pressure resistant body. The stabilization apparatus, however, fails to be torsionally stiff and does not allow for axial extension. In addition, the use of monoaxial pedicle screws limits the application of this stabilization apparatus.

US 2007/0093820 A1 discloses a dynamic spinal stabilization comprising a flexible rod made of an elastomer material which is clamped in the receiving parts of monoaxial bone screws. EP 1 795 134 A1 and EP 1 900 334 A1 describe a spinal stabilization system with a flexible elastomer rod and polyaxial bone screws.

The dynamic stabilization systems comprising a flexible elastomer rod are suitable for the control, in particular the damping, of axial compression and extension of motion segments of the spinal column. The elastomer material is advantageous with respect to obtaining the suitable length of the rod-shaped implant by cutting an elastomer rod and the implant is simple to manufacture.

In clinical cases of early degeneration or partial damages or injuries of intervertebral discs the corresponding motion segments of the spinal column are subject to increased rotational movements and shearing forces. Such rotational movements and shearing forces can cause strong pain.

US 2007/049937 A1 discloses a rod-shaped implant which includes a metallic hollow rod with a flexible section in form of a helix-shaped recess in wall of the rod. In the hollow rod a longitudinal core is provided which can be fixed with respect to one end of the rod and which can be moveable with respect to the other end of the rod. The problem of kinking of the rod-shaped implant caused by shearing movements of the spinal column is considerably reduced.

Based on the foregoing, there is a need to provide an implant and a stabilization system for the spinal column which is particularly suited for cases in which rotational and shearing movements of the spinal column shall be suppressed.

SUMMARY

The rod-shaped implant according to the disclosure includes a flexible rod made at least partly of an elastomer material and further includes a reinforcing rod for strengthening the implant in particular against rotational movements of the spinal column in an axial direction and against shearing forces. The spinal stabilization system includes such a rod-shaped implant and at least two bone anchoring elements to be connected to the rod-shaped implant.

The rod-shaped implant according to the disclosure uses an elastomer rod but has enhanced stability compared to purely elastomeric rods and is a modular system allowing various combinations of elastomeric rods and reinforcing rods.

The rod-shaped implant and the stabilization system allows a dynamic damping of the axial tension and compression movements by using the elastomer rod and considerably enhances the resistance against rotational and/or shearing and/or bending movements due to the reinforcing rod.

BRIEF DESCRIPTION OF THE DRAWINGS

FIG. 3 shows a schematic perspective view of a bone anchoring element which is adapted to the rod-shaped implant.

FIG. 4 shows a schematic sectional view of the bone anchoring element of FIG. 3 with an inserted rod-shaped implant, the section being taken perpendicular to the rod axis.

FIG. 5 shows a schematic sectional view of the bone anchoring element of FIG. 3 with a modified rod-shaped rod-implant.

FIG. 6 shows a schematic sectional view of the bone anchoring element of FIG. 3 with a still further modified rod-shaped implant.

DETAILED DESCRIPTION

Figure 1:
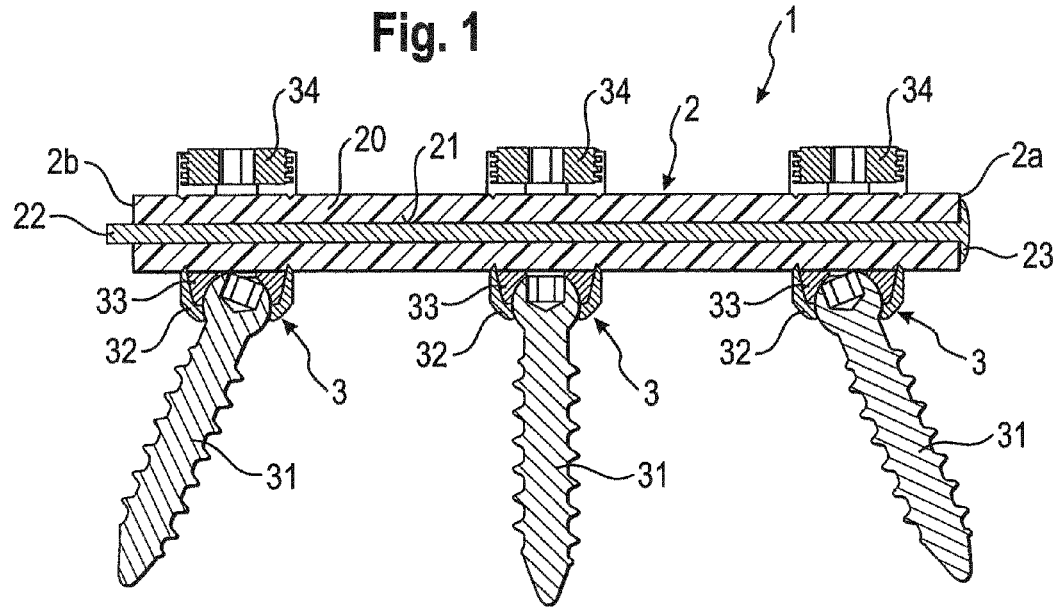
FIG. 1 shows a schematic sectional view of the stabilization system, the section being taken along the rod axis.
Figure 2:
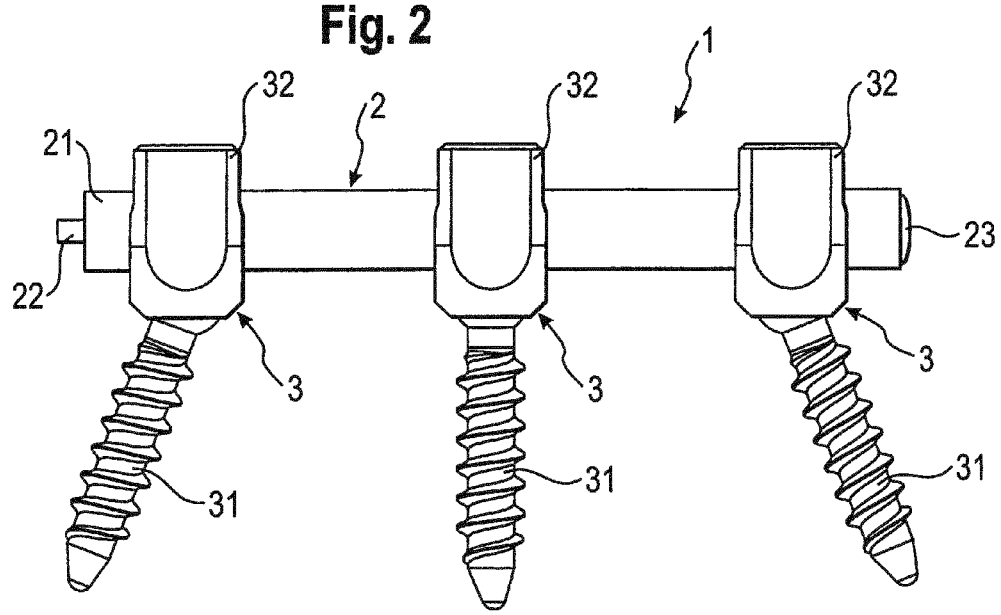
FIG. 2 shows a schematic side view of the stabilization system.

As shown in FIGS. 1 and 2, the stabilization device 1 includes a rod-shaped implant 2 and a plurality of bone anchoring elements 3. The bone anchoring elements can be anchored in bony structures, in particular in adjacent vertebrae of the spinal column. The rod-shaped implant 2 can be connected to the bone anchoring elements so that it is anchored in the vertebrae. Hence, the total length of the rod-shaped implant 2 is such that it spans the distance of at least two vertebrae of the spinal column.

In the embodiment shown, the rod-shaped implant is formed of a cylindrical rod 20 comprising a first end 2a and a second end 2b. A coaxial bore 21 extends from the first end 2a to the second 2b through the cylindrical rod 20. In this embodiment the coaxial bore has a circular cross section.

In the coaxial bore 21 a reinforcing rod 22 is accommodated which has a circular cross section and a diameter which is sized such that the reinforcing rod 22 can slide within the coaxial bore 21. The reinforcing rod 22 extends from the first end 2a to at least the second end 2b and may project beyond second end 2b of the cylindrical rod 20. At one end, for example at the first end 2a, the reinforcing rod 22 is limited with respect to its movement relative to the rod 20 with a stop 23. The stop 23 can be formed, for example, as a disc which is mounted to the end of the reinforcing rod. Other constructions for the stop 23 are conceivable. For example, the stop can be adjustable along an end portion of the reinforcing rod 22. This can be realized, for example, by providing a thread on the outer surface of the end portion of the reinforcing rod 22 and by providing a nut to be screwed on the threaded end portion which abuts against the end 2a of the cylindrical rod 22 (not shown).

Figure 9:
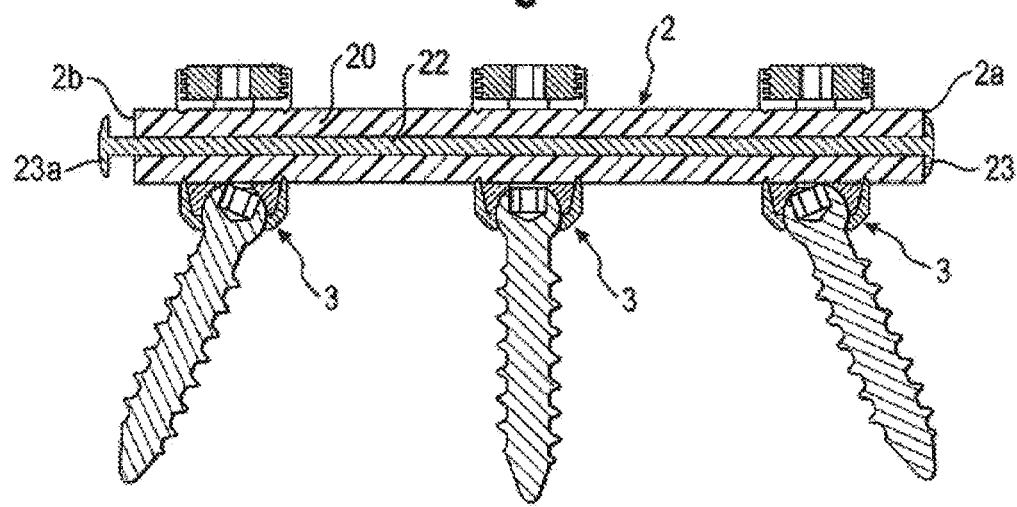
FIG. 9 shows a schematic sectional view of a stabilization system having a rod-shaped implant with a second stop, the section being taken along the rod axis.

The reinforcing rod is movable at the second end 2b. However, a second stop 23a can be provided also at a distance from the second end 2b, for example, as shown in FIG. 9. The second stop may be adjustable. If a second stop is provided, the distance between the first stop and the second stop is greater than the distance between the first end 2a and the second end 2b so that the reinforcing rod 22 is freely movable.

The material of the rod 20 is a plastic material which exhibits flexibility when the rod 20 experiences compression or tension forces acting in an axial direction. Particularly suitable are polymer materials exhibiting such flexibility, preferably elastomer materials such as polyurethanes, polycarbonate urethanes (PCU) or polysiloxanes. Any other material exhibiting such elastic features is, however, suitable. Since the material exhibits flexible properties, the cylindrical rod 20 also reacts on rotational forces around the rod axis and on shearing forces having a component perpendicular to the rod axis. Such forces arise from torsional and shearing motions of the motion segments of the spine.

In order to control and dampen such rotational and shearing forces the reinforcing rod 22 is made from a material which is less flexible than the cylindrical rod 20 or which exhibits no flexibility under forces acting along the rod axis. Particularly suitable materials are body compatible metals, such as stainless steel or titanium or titanium alloys, such as Nitinol, or rigid plastic materials, for example PEEK or carbon fiber reinforced PEEK or others.

The reinforcing rod 22 can be coated to facilitate sliding within the coaxial bore of the cylindrical rod 20. Alternatively a sliding guidance or a sliding bearing can be provided to facilitate sliding of the reinforcing rod.

The bone anchoring element 3 can be any monoaxial bone screw or bone hook, but is preferably a polyaxial bone screw as depicted in FIGS. 1 and 2. The polyaxial bone screw 3 includes a screw element 31 with a threaded shank and a spherically shaped head which is pivotably held in a receiving part 32 which receives the rod. To fix the screw element 31 in a desired angular position with respect to the receiving part 32 a pressure element 33 acting onto the head of the screw element 31 is provided. The rod-shaped implant 2 is received in the receiving part 32 and is fixed with a fixation element 34.

FIGS. 3 and 4 show a bone anchoring element 30 which is specifically adapted for use with the rod-shaped implant. The bone anchoring element 30 includes a screw element 31 with a threaded shank and a spherically-shaped head and a receiving part 32 for receiving the rod-shaped implant 2. The receiving part 32 is substantially cylindrical or cuboid-shaped and includes a coaxial bore 32a which extends from one end to the opposite end and which tapers with respect to one end in order to pivotably accommodate the screw head of the screw element 31. The receiving part 32 further includes a U-shaped recess 32b for receiving the rod-shaped implant 2.

A first pressure element 33 is provided which is substantially cylindrical and movable in the bore. It presses onto the head of the screw element and has a U-shaped recess 33b to accommodate the rod-shaped implant 2. The U-shaped recess 33b has a depth such that the pressure element extends above the surface of the rod-shaped implant 2 when the rod-shaped implant 2 is inserted.

A fixation screw 34 is provided which can be screwed into the receiving part 32 from the free ends of the U-shaped recess 32b.

Furthermore, a second pressure element 35 is provided which can be pressed downwards with the fixation screw 34.

The first pressure element 33 and the second pressure element 35 are shaped in such a way that the rod-shaped implant 2 is enclosed therebetween and fixed in an axial direction without pressing onto the reinforcing rod 22. Therefore, the reinforcing rod is still moveable. The fixation screw 34 also presses onto the first pressure element 33 in order to fix the head of the screw element 31 in the receiving part, independently from the fixation of the rod-shaped implant.

The surfaces of the first pressure element 33 and the second pressure element 35 which contact the rod-shaped implant may have engagement structures engaging the surface of the rod without harming the surface structure of the rod-shaped implant.

FIGS. 5 and 6 show variations of the cross-section of the reinforcing rod and the corresponding bore in the elastomer rod 20. In FIG. 5 a modified rod-shaped implant 2' is shown which differs from the rod-shaped implant 2 of the previous embodiment in that the cross-section of the reinforcing rod 22' is rectangular and the corresponding bore in the rod 20 has also a rectangular cross-section. In the embodiment shown in FIG. 5 the rod-shaped implant 2' is arranged such that the long side of the rectangle of the reinforcing rod 22' is aligned perpendicular to the axis of the screw element 31. However, any other orientation is possible. In the modification shown in FIG. 6 the cross-section of the reinforcing rod 2' is cross-shaped.

Other cross-sections of the reinforcing rod are conceivable, for example a polygon-shaped cross-section. The resistance against rotational and/or shearing forces and/or bending forces can be enhanced by using a reinforcing rod with a non-circular cross-section. In addition, if necessary, the rod-shaped implant can be provided with an orientation dependent bending flexibility by using a reinforcing rod with a non-circular cross-section.

Figure 7:
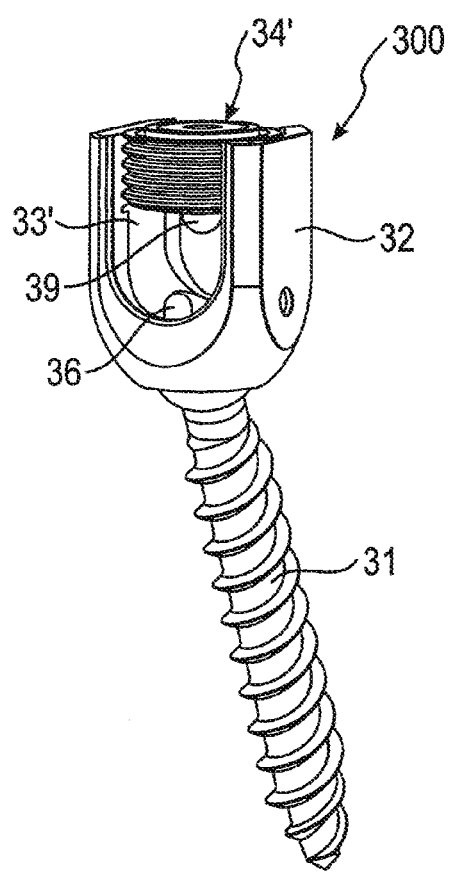
FIG. 7 shows a schematic perspective view of a bone anchoring element which is modified concerning the adaptation to the rod-shaped implant.
Figure 8:
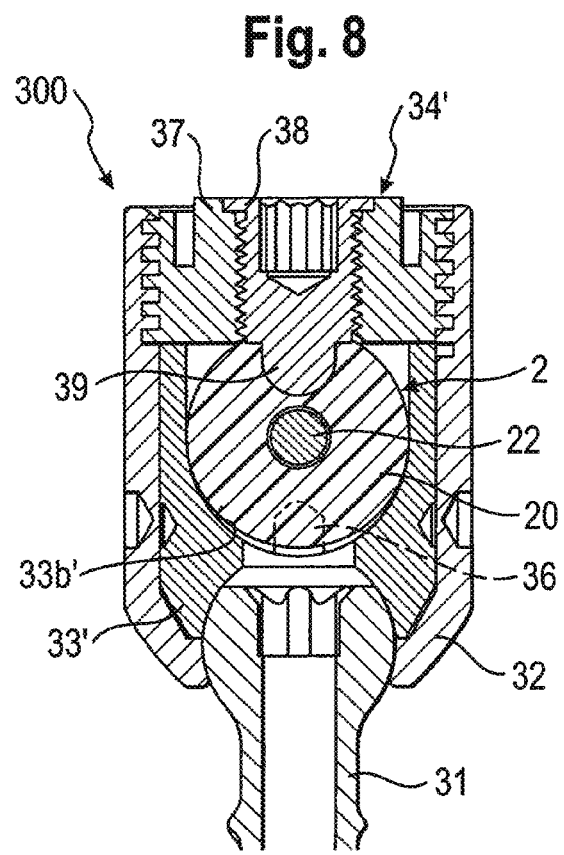
FIG. 8 shows a schematic sectional view of the bone anchoring element of FIG. 7 with the rod-shaped implant inserted, the section being taken perpendicular to the rod axis.

FIGS. 7 and 8 show a modified bone anchoring element 300 which differs from the bone anchoring element 30 in that the pressure element 33' has a U-shaped recess 33b' which has a depth such that the pressure element projects only slightly above the surface of the rod-shaped implant 2 when the rod-shaped implant is inserted. On the bottom of the U-shaped recess one or several pin-shaped projections 36 are provided which engage the surface of the rod-shaped implant 2.

The fixation element 34' is a two-part fixation element with an outer screw 37 and an inner screw 38. The outer screw 37 is screwed into the receiving part 32 and presses onto the pressure element 33' in order to lock the angular position of the screw element 31 in the receiving part. The inner screw 38 has a pin-shaped projection 39 on its side facing the rod-shaped implant 2. The inner screw 38 together with the projection 36 clamp the rod-shaped implant 2 independently of the fixation of the head of the screw element 31 in the receiving part 32. The dimension of the pin-shaped projections 36 and 39 and the dimension of the inner and outer screw of the fixation element 34' is such that only the rod 20 is clamped whereas the reinforcing rod 22 is still freely movable.

In use, first at least two bone anchoring elements are inserted into the respective vertebrae. Thereafter, the necessary length of the rod-shaped implant is determined and an appropriate rod-shaped implant is cut from the rod consisting of the elastomer rod with the reinforcing rod. If necessary, a stop is included at one or both ends.

Thereafter, the rod-shaped implant is inserted into the receiving parts of the bone anchoring elements. Then, the vertebrae are adjusted in their position with respect to each other and the polyaxial position of the screw element 31 with respect to the receiving parts is locked. After adjusting the distances of the receiving parts the rod-shaped implant is fixed.

While a particular form of the disclosure has been illustrated and described, it will be apparent that various modifications can be made without departing from the spirit and scope of the disclosure. Accordingly, it is not intended that the disclosure be limited, except as by the appended claims.

What is claimed is:

1. A spinal stabilization system for stabilizing bone structures or a spinal column, the spinal stabilization system comprising:
   at least one bone anchoring element comprising a receiving part; and
   a rod-shaped implant configured to be inserted in the receiving part, the rod-shaped implant comprising:
      a monolithic rod-shaped member made of an elastomer material and having a first end, a second end, and a bore extending from the first end toward the second end along a longitudinal axis of the rod-shaped member, wherein the bone anchoring element is connectable directly to the rod-shaped member at a first location adjacent the first end and is connectable directly to the rod-shaped member at a second location adjacent the second end, and wherein the rod-shaped member comprises a tube with a solid annular wall extending from the first location to the second location; and
      a reinforcing rod comprising a body compatible metal or a body compatible rigid plastic material that is more rigid than the material of the rod-shaped member, the reinforcing rod having a first end and a second end;
   wherein when the spinal stabilization system is implanted, a first stop is fastened to the first end of the reinforcing rod to prevent relative movement between the first stop and the reinforcing rod, while the reinforcing rod is accommodated in and remains slidable in the bore of the rod-shaped member; and
   wherein the first stop is configured to engage and disengage the first end of the rod-shaped member to limit the sliding movement of the reinforcing rod relative to the rod-shaped member.

2. The spinal stabilization system according to claim 1, wherein the bore of the rod-shaped member extends from the first end to the second end of the rod-shaped member.

3. The spinal stabilization system according to claim 1, wherein the first stop limits the sliding motion of the reinforcing rod with respect to the first end of the rod-shaped member while the reinforcing rod is movable with respect to the second end of the rod-shaped member.

4. The spinal stabilization system according to claim 1, further comprising a second stop at the second end of the reinforcing rod and located at a distance from the second end of the rod-shaped member along the longitudinal axis when the first stop and the first end of the rod-shaped member are engaged.

5. The spinal stabilization system according to claim 1, wherein a cross-section of the reinforcing rod is non-circular.

6. The spinal stabilization system according to claim 1, wherein the material of the rod-shaped member exhibits flexibility when compression or extension forces are applied along the longitudinal axis.

7. The spinal stabilization system according to claim 1, wherein means for facilitating sliding of the reinforcing rod are provided.

8. The spinal stabilization system according to claim 1, wherein the reinforcing rod and the first stop are formed as a monolithic member.

9. The spinal stabilization system according to claim 1, wherein in a first position the first end of the rod-shaped member is engaged with the first stop while an end face at the second end of the rod-shaped member is spaced apart from all other portions of the rod-shaped implant along the longitudinal direction, and wherein in a second position the first end of the rod-shaped member is disengaged with the first stop while the end face at the second end of the rod-shaped member remains spaced apart from all other portions of the rod-shaped implant along the longitudinal direction.

10. The spinal stabilization system according to claim 1, wherein the rod-shaped member has a constant cross-section along the longitudinal axis from the first location to the second location of the rod-shaped member.

11. The spinal stabilization system according to claim 1, wherein the rod-shaped member has a first length from the first end to the second end when the rod-shaped member is unbiased, and wherein a region of the reinforcing rod slidable in the bore is greater than the first length.

12. The spinal stabilization system according to claim 1, wherein when the first end of the rod-shaped member is engaged with the first stop, a region of the reinforcing rod slidable in the bore extends past the second end of the rod-shaped member in a direction away from the first stop.

13. A spinal stabilization device comprising:
   a rod-shaped implant comprising:
      a monolithic rod-shaped member made of an elastomer material and having a first end, a second end, and a bore extending from the first end toward the second end along a longitudinal axis of the rod-shaped member;
      a reinforcing rod comprising a body compatible metal or a body compatible rigid plastic material that is more rigid than the material of the rod-shaped member, the reinforcing rod having a first end and a second end; and
      a first stop at the first end of the reinforcing rod;
      wherein when the spinal stabilization device is implanted, the reinforcing rod is accommodated in and remains slidable in the bore of the rod-shaped member; and
      wherein the first stop is configured to contact the rod-shaped member to limit movement of the reinforcing rod relative to the rod-shaped member; and
   at least two bone anchoring elements respectively connected at a first location and a second location of the rod-shaped member, each bone anchoring element comprising a receiving part in which the rod-shaped member is received, wherein the rod-shaped member comprises a tube with a solid annular wall extending from the first location to the second location.

14. The spinal stabilization device according to claim 13, wherein at least one of the bone anchoring elements is a polyaxial screw comprising a screw element which can be pivoted in the receiving part.

15. The spinal stabilization device according to claim 14, wherein the polyaxial screw is configured such that a position of the screw element with respect to the receiving part can be locked independently from fixation of the rod-shaped member to the receiving part.

16. The spinal stabilization device according to claim 13, wherein the reinforcing rod is movable relative to the rod-shaped member when the rod-shaped member is fixed to the receiving parts.

17. The spinal stabilization device according to claim 13, wherein at least one of the receiving parts comprises projections configured to engage a surface of the rod-shaped member to deform the surface of the rod-shaped member to fix the rod-shaped member to the receiving part, wherein the surface of the rod-shaped member is not harmed by the deformation.

18. The spinal stabilization device according to claim 13, further comprising a second stop at the second end of the reinforcing rod and spaced apart from the second end of the rod-shaped member when the first stop is contacting the first end of the rod-shaped member.

19. A method of stabilizing a spine with a spinal stabilization device comprising two bone anchoring elements and a rod-shaped implant, the rod-shaped implant comprising a monolithic rod-shaped member made of an elastomer material and having a first end, a second end, and a bore extending from the first end toward the second end along a longitudinal axis of the rod-shaped member, a reinforcing rod comprising a body compatible metal or a body compatible rigid plastic material that is more rigid than the material of the rod-shaped member, the reinforcing rod having a first end and a second end, and a stop at the first end of the reinforcing rod, wherein when the spinal stabilization device is implanted, the reinforcing rod is accommodated in and remains slidable in the bore of the rod-shaped member, and wherein the stop is configured to contact the rod-shaped member to limit movement of the reinforcing rod relative to the rod-shaped member, and wherein each bone anchoring element comprises a receiving part in which the rod-shaped member is received, the method comprising:

attaching the first bone anchoring element to a bone or vertebra;

attaching the second bone anchoring element to a bone or vertebra;

fixing the rod-shaped member with an inserted reinforcing rod to the receiving part of the first bone anchoring element at a first location of the rod-shaped member; and fixing the rod-shaped member to the receiving part of the second bone anchoring element at a second location of the rod-shaped member, wherein the rod-shaped member comprises a tube with a solid annular wall extending from the first location to the second location.

20. The method of claim 19, further comprising inserting the reinforcing rod in the bore of the rod-shaped member before fixing the rod-shaped member to the first and second bone anchoring elements.

* * * * *

UNITED STATES PATENT AND TRADEMARK OFFICE
CERTIFICATE OF CORRECTION

PATENT NO. : 9,451,988 B2  Page 1 of 1
APPLICATION NO. : 12/550960
DATED : September 27, 2016
INVENTOR(S) : Lutz Biedermann et al.

It is certified that error appears in the above-identified patent and that said Letters Patent is hereby corrected as shown below:

On the Title Page

(73) Assignee    Delete "Donauschingen",
                 Insert --Donaueschingen--

Signed and Sealed this
Sixteenth Day of May, 2017

Michelle K. Lee
*Director of the United States Patent and Trademark Office*